United States Patent [19]

Khan et al.

[11] Patent Number: 5,547,662
[45] Date of Patent: Aug. 20, 1996

[54] PREPARATION OF A SKIN SURFACE FOR A SURGICAL PROCEDURE

[75] Inventors: Mohammad A. Khan, Sandy; Minh Q. Hoang, Taylorsville, both of Utah

[73] Assignee: Becton, Dickinson and Company, Franklin Lakes, N.J.

[21] Appl. No.: 113,445

[22] Filed: Aug. 27, 1993

[51] Int. Cl.⁶ ............... A41D 13/10; A41D 19/00
[52] U.S. Cl. ............ 424/78.03; 424/78.02; 424/78.06; 424/78.07
[58] Field of Search ............ 424/78.03, 78.36, 424/78.37, 401

[56] References Cited

U.S. PATENT DOCUMENTS

| | | | |
|---|---|---|---|
| 4,374,128 | 2/1983 | Cardarelli et al. | 424/81 |
| 4,542,012 | 9/1985 | Dell | 424/28 |
| 5,173,291 | 12/1992 | Brink et al. | 424/78.07 |
| 5,335,373 | 8/1994 | Dangman | 2/161.7 |

*Primary Examiner*—Sharon Gibson
*Assistant Examiner*—Catherine Kilby Scalzo
*Attorney, Agent, or Firm*—Arthur D. Dawson

[57] ABSTRACT

A film forming composition for preparation of a skin surface as a surgical site includes a film forming material and a antimicrobial agent soluble in a fugitive solvent. The composition when applied to the skin surface forms a substantially water insoluble, substantially tack-free flexible film adherent to the skin surface. The film is capable of releasably retaining the antimicrobial agent to substantially inhibit microbial growth on the skin surface. The film releases sufficient antimicrobial agent to substantially eliminate the microorganisms normally present on the skin surface to prepare the surface for the procedure and continues to release the antimicrobial agent during the procedure and subsequent wound healing. A preferred embodiment of the composition includes at least one compound for providing a first color indicative of the skin surface area covered by the composition and develops a second color upon the substantial elimination of the fugitive solvent indicating that the site is ready. A method for use of the composition to prepare a skin surface for a surgical procedure includes providing the composition, observing the first color for indicating the skin area covered and the second color indicating that the fugitive solvent has substantially evaporated. A single use kit for preparing a skin surface for a surgical procedure includes a non-resealable unit container of the film forming composition and an applicator in a non-resealable package.

20 Claims, No Drawings

PREPARATION OF A SKIN SURFACE FOR A SURGICAL PROCEDURE

FIELD OF INVENTION

This invention relates to a kit, a film forming composition and a method for surgical site preparation on skin surface. More specifically the invention relates to a film forming composition having an antimicrobial agent that is released onto the skin.

BACKGROUND OF THE INVENTION

The normal surface of the skin has a multiplicity of microorganisms on it. As long as the skin surface is intact, the microorganisms generally present no problem to the body, achieving some natural balance with each other. When a surgical procedure is conducted which breaches the natural barrier formed by the skin, it is important that these normally present microorganisms be prevented from entering the wound. Various protocols to reduce or eliminate skin microorganisms have been developed and are generally practiced rigorously. The protocols generally involve a thorough scrubbing of the skin surface with an antimicrobial agent, possibly shaving the area if hair is present, and draping the patient with sterile drapes so that only the immediate area of the procedure is exposed. Following the procedure, the wound area is covered with a dressing for isolation until healing is substantially complete.

These procedures are generally successful, with the occurrence of post-surgical infections being maintained at a low level in most institutions. The goal of all these practices is to rapidly decrease the microbial count present on the skin, then prevent regrowth of the organisms during the period when the surgical site is open and during the subsequent healing process.

Many of the common protocols require scrubbing the surgical site with isopropyl alcohol for a prescribed time or scrubbing the site with an iodophor such as polyvinylpyrrolidone iodine or other antimicrobial agent. The area is then draped with sterile drapes leaving only the actual surgical field area exposed. During the procedure, the freshly scrubbed site may be subjected to blood, various body fluids and saline washes coupled with mechanical abrasion by sponges and the like. The effect of these washes may be to remove any residual antimicrobial agent, reinfect the surface and allow a regrowth of microorganisms that potentially may enter the open wound. Several workers have addressed the problem of surgical site preparation by incorporation of an antimicrobial agent into a material that forms a film when applied to skin surface. Cardelli et al. U.S. Pat. No. 4,374,126 teaches a composition and method for forming a film from an alcohol soluble carboxylated polyacrylate which includes an antimicrobial agent, an adhesion promoter and a difunctional amide for crosslinking the polymer as the alcohol solvent evaporates. The film formed is thus resistant to body fluids, can remain on the skin for up to two days providing both initial and sustained anti-microbial activity.

Dell U.S. Pat. No. 4,542,012 teaches a film forming polymer containing complexed iodine as a broad spectrum antimicrobial agent. The composition is applied to the skin from a volatile solvent, which when evaporated, leaves the iodine containing polymer film. The iodine is released from the film to provide antimicrobial action.

Brink U.S. Pat. No. 5,173,291 teaches an iodine containing aqueous polymer emulsion which forms a film when applied to the skin surface. The film releases the iodine as an antimicrobial agent.

These cited examples provide improvements to surgical site preparation procedures. However, unless iodine is used as the antimicrobial agent, it is often difficult to visualize the area to which the film has been applied. Iodine, while effective as an antimicrobial agent, may cause tissue reactions and staining. Additionally, in many of the film forming agents available, it is difficult to visually determine when the application solvent has sufficiently evaporated to begin the procedure. Often a practitioner will physically touch the surface to see if it is dry. If the surface is not dry, such a touch may initiate a breach in the film which may provide a pathway for microorganisms. Thus there is a need for a composition for preparation of a surgical site by forming a film containing an antimicrobial agent which provides visual indication of the area to which the composition has been applied. If the composition also provided an indication when the delivery solvent was substantially eliminated, the practice of surgical site preparation would be further advanced.

SUMMARY

A film forming composition for surgical site preparation on a skin surface includes a fugitive solvent, a film forming material which is soluble in the fugitive solvent, and an antimicrobial agent which is soluble in the solvent as well as capable of being releasably retained in the film forming material. The film forming material and the antimicrobial agent are dissolved in the fugitive solvent for application to the surface area of the skin intended as a surgical site. As the fugitive solvent evaporates, the film forming material forms a substantially water insoluble, substantially tack-free flexible film which is adherent to the skin surface. The film is capable of releasing the antimicrobial agent and substantially inhibiting microbial growth on the skin surface during the procedure and subsequent wound healing. Preferably, the composition further includes a plasticizing agent to increase the flexibility of the film. Preferably, the composition also includes an indicating component to provide a first color to define the applied area and a second color to indicate when the fugitive solvent is substantially eliminated. The development of the second color provides a visual indication that the surface is dry and ready for the surgical procedure.

Desirably, the antimicrobial agent is present in a quantity sufficient to inhibit microbial growth on the surface of the skin. The antimicrobial agent may include, but is not limited to, iodophors, chlorphenols, biguanides, antibiotics and their biologically active salts. Preferably, the antimicrobial agent is chlorhexidine diacetate.

Desirably, the film forming material is an organic polymeric material such as ethyl cellulose, methoxycellulose, hydroxyethylcellulose, polyvinylpyrrolidone/vinyl acetate copolymer and crosslinked pyrrolidone. Preferably the film forming material is ethyl cellulose.

The fugitive solvent is a liquid that has appreciable volatility in the range 25° to 40° C. such as isopropanol, ethanol, ethylene dichloride, acetone, ethyl acetate, 1,1,2-trichloro-trifluoroethane and the like which is capable of dissolving the components of the composition. Preferably, the fugitive solvent is isopropyl alcohol.

A method for preparing a skin surface as a site for a surgical procedure includes preparing a film forming composition as a homogeneous solution of a fugitive solvent, a material for forming a film and an antimicrobial agent soluble in the solvent as well as capable of being releasably retained in the film forming material. After applying the composition to cover the skin site selected for the procedure, and allowing the solvent to evaporate, the surgical site is ready for the procedure. Preferably the film forming composition includes at least one compound which provides the composition with a first color indicating the area of the skin covered and, as the solvent is eliminated, develops a second color providing the user with a visual indication that the film has dried. This color change suggests that the surgical site is ready for the procedure.

A kit to prepare a skin surface for a surgical procedure preferably includes a sealed unit dose container of a film forming composition prepared from a homogeneous solution of a film forming material, an antimicrobial agent and a fugitive solvent. The kit also includes an applicator for applying the film forming composition to the skin surface. The kit further includes a package for holding the container and the applicator. In a preferred embodiment, the film forming composition includes an indicating component which provides a first color to define the applied area and a second color for indicating when the fugitive solvent is substantially eliminated. The preferred embodiment also includes provisions for rendering the container for the film forming composition and the package for holding the container and the applicator non-resealable.

DETAILED DESCRIPTION

While this invention is satisfied by embodiments in many different forms, there will be described herein in detail embodiments of the invention, with the understanding that the present disclosure is to be considered as exemplary of the principles of the invention and is not intended to limit the invention to the embodiments described. The scope of the invention will be measured by the appended claims and their equivalents.

A film forming composition for surgical site preparation on a skin surface includes a fugitive solvent, a film forming material soluble in the solvent and an antimicrobial agent soluble in the solvent as well as capable of being releasably retained in the film forming material. The film forming material and the antimicrobial agent are applied to the skin surface from the fugitive solvent and form a substantially water insoluble, substantially tack-free flexible film which is adherent to the skin surface. The film releases the antimicrobial agent onto the skin surface thus substantially eliminating microbial growth on the skin surface during the procedure and during wound healing. Preferably the composition includes a plasticizing agent to increase the flexibility of the film. A further desirable embodiment of the composition includes incorporation of at least one compound which indicates the surface area of the skin covered by the composition and additionally indicates when the fugitive solvent is substantially eliminated.

A preferred embodiment of the composition includes compounds which provide a first color which visually indicates the skin area covered by the composition and a second color which gives a visual indication that the fugitive solvent has been substantially eliminated.

The term "fugitive solvent" as used herein describes a solvent having an appreciable vapor pressure, hence it is volatile, at temperatures between about 25° C. and about 40° C. Suitable fugitive solvents are alcohols, esters, chlorinated hydrocarbons, esters and chlorofluorocarbons. Exemplary fugitive solvents include isopropanol, ethanol, ethyl acetate, trichloroethane, acetone and 1, 1,2-trichlorotrifluoroethane.

Suitable antimicrobial agents include iodophors, chlorophenols, biguanides, antibiotics and biologically active salts. These agents may be incorporated into the composition in a quantity sufficient to substantially inhibit microbial growth on the surface of the skin. Some of the antimicrobial agents impart a color to the composition and would be inherently indicative of the covered area of the skin surface.

In a preferred embodiment of the composition having chlorhexidine diacetate as the antimicrobial agent, color is imparted to the composition preferably by including orthophenylphenol, sodium salt, in combination with a suitable dye such as Food, Drug and Cosmetic Red No. 40 and Drug and Cosmetic Red No. 17. These compounds provide a first color (purple) for indicating the surface of the skin covered by the composition and a second color (red) which is indicative of the substantial elimination of the fugitive solvent.

Suitable film forming materials include but are not limited to ethyl cellulose, methoxycellulose, hydroxyethyl cellulose, polyvinylpyrrolidone/vinyl acetate copolymer and crosslinked pyrrolidone. A preferred composition includes ethyl cellulose having an ethoxy content between about 45 percent to about 55 percent.

Plasticizing agents desirably are added to the composition to impart flexibility to the film. Suitable plasticizing agents include but are not limited to polyethylene glycol, polyoxyethylene propylene glycol, polyoxypropylene glycol, polyoxyethylene polyoxypropylene block copolymers, glycerin and various vegetable oils such as cottonseed oil, palm oil, rapeseed oil, sunflower oil, castor oil and the like. In the preparation and examination of film forming compositions it was discovered that the rate of release of antimicrobial agents from the film depends upon the nature of the plasticizing agent used. Hydrophobic plasticizing agents, such as the vegetable oils, tended to impede the rate of release of the antimicrobial agent while the hydrophilic materials such as polyoxypropylene glycol, polyethylene glycols and polyoxyethylene tended to enhance the rate of release of the antimicrobial agents from the film.

There are several benefits of having an indicator system in the film forming composition. While some compounds used as antimicrobial agents, such as iodophors, are inherently colored, others, which in many cases are at least equally effective and less irritating, are substantially colorless. It is believed that while solvated, orthophenyl phenol, sodium salt and the dye form a complex, and as the solvent is eliminated, the complex shifts the wavelength of the light absorbed, thus changing the color of the complex. Incorporation of an indicator which imparts a color to the composition allows the practitioner to ensure complete coverage of the site. Further, having an indicator system which has a first color for indicating coverage and a second color which indicates the substantial elimination of the fugitive solvent allows the practitioner to know that the film is dry and the site is ready for the planned procedure to begin. Prior to the present invention, the practitioner would have to touch the surface to see if it was dry. If the film was not dry, a touch could cause a weak spot in the film, possibly leading to a breach in the film or contamination of the surgical site.

The following example compositions are provided to illustrate the invention, but are not to be considered to be limitative of the invention. Table I lists a number of components and their sources for reference to the example compositions, which follow.

TABLE I

| Ingredient | Grade/Source |
| --- | --- |
| castor oil | U.S.P. Grade or equivalent |
| chlorhexidine diacetate | British Pharmacopoeia Grade, Degussa, Ridgefield Park, NJ |
| cotton seed oil | U.S.P. Grade or equivalent |
| Drug and Cosmetic (D. and C.) red No. 17 | Tricon Colors Inc., Elmwood Park, NJ |
| ethyl alcohol | SD-40, National Formulary |
| ethyl cellulose | ethyl cellulose with ethoxy content 48.0–49.5%, Ethocel standard No. 7, Dow Chemical, Midland, MI |
| Food, Drug and Cosmetic (F.D. and C) red No. 40 | IMton-Davis, Cinn. OH |
| glycerin | U.S.P. grade or equivalent |
| pentahexylmethylene biguanide hydrochloride | Cosmocil, ICI, Wilmington, DE |
| iodine | U.S.P. grade or equivalent |
| isopropyl alcohol | U.S.P. grade or equivalent |
| N,N$^1$-(1,10-decanediyldi-1[4H]-pyridinyl-4-)-(1-octanamine) dihydrochloride | Neokodan, Schülke & Mayr, GMBH, Germany |
| orthophenyl phenol, sodium salt | Dowacide A, Dow Chemical, Midland, MI |
| polyoxypropylene glycol | Pluronics, BASF, Wyandotte, MI |
| L-31 | L-31 molecular weight 950 plus four moles ethylene oxide |
| L-101 | L-101 molecular weight 3250 plus fourteen moles ethylene oxide |
| poly(tetrahydrofuran) | Molecular Weight 1000, Aldrich, Milwaukee, WI |
| propylene glycol methyl ether | 1-methoxy-2-2-propanol, Dowanol P.M., Dow Chemical Midland, MI |
| para-chloro-meta-xylenol (p-chloro-m-xylenol) | Ferro Chemical, Ottawa, OH |

EXAMPLE I

| Ingredient | Amount (Weight/Weight [wt./wt.], Parts Per Hundred) |
| --- | --- |
| ethyl cellulose | 3.32 |
| propylene glycol methyl ether | 50.87 |
| isopropyl alcohol | 43.40 |
| chlorhexidine diacetate | 0.12 |
| castor oil | 2.21 |
| F.D. and C. red No. 40 | 0.08 |

The ingredients were thoroughly mixed to a homogenous solution by stirring at ambient temperature, then stored in a closed vessel.

EXAMPLE II

| Ingredient | Amount (wt./wt., Parts Per Hundred) |
| --- | --- |
| ethyl cellulose | 3.50 |
| propylene glycol methyl ether | 15.00 |
| isopropyl alcohol | 77.85 |
| polyoxypropylene glycol L-101 | 2.00 |
| polyoxypropylene glycol L-31 | 0.30 |
| chlorhexidine diacetate | 1.00 |
| D. and C. red No. 17 | 0.05 |
| orthophenylphenol, sodium salt | 0.30 |

The ingredients were thoroughly mixed to a homogeneous solution by stirring at ambient room temperature, then stored in a closed vessel.

EXAMPLE III

| Ingredient | Amount (wt./wt., Parts Per Hundred) |
| --- | --- |
| ethyl cellulose | 3.50 |
| propylene glycol methyl ether | 15.00 |
| isopropanol | 78.15 |
| chlorhexidine diacetate | 1.00 |
| D. and C. Red No. 17 | 0.05 |
| orthophenylphenol, sodium salt | 0.30 |
| cottonseed oil | 2.00 |

The ingredients were thoroughly mixed to a homogenous solution by stirring at ambient temperature, then stored in a closed vessel.

EXAMPLE IV

| Ingredient | Amount (wt./wt., Parts Per Hundred) |
| --- | --- |
| ethyl cellulose | 3.50 |
| propylene glycol methyl ether | 15.00 |
| isopropanol | 78.15 |
| chlorhexidine diacetate | 1.00 |
| D. and C. red no. 17 | 0.05 |
| orthophenylphenol, sodium salt | 0.30 |
| castor oil | 2.00 |

The ingredients were thoroughly mixed to a homogeneous solution by stirring at ambient temperature, then stored in a closed vessel.

EXAMPLE V

| Ingredient | Amount (wt./wt., Parts Per Hundred) |
| --- | --- |
| ethyl cellulose | 3.50 |
| propylene glycol methyl ether | 15.00 |
| isopropanol | 78.15 |
| chlorhexidine diacetate | 1.00 |
| D. and C. red no. 17 | 0.05 |
| orthophenylphenol, sodium salt | 0.30 |
| glycerin | 2.00 |

The ingredients were thoroughly mixed to a homogenous solution by stirring at ambient temperature, then stored in a closed vessel.

EXAMPLE VI

| Ingredient | Amount (wt./wt., Parts per hundred) |
| --- | --- |
| ethyl cellulose | 3.50 |
| propylene glycol methyl ether | 15.00 |
| isopropanol | 76.15 |
| chlorhexidine diacetate | 1.00 |
| D. and C. red no. 17 | 0.05 |
| orthophenylphenol, sodium salt | 0.30 |
| polyoxypropylene glycol L-101 | 2.00 |
| poly (tetrahydrofuran) | 2.00 |

The ingredients were thoroughly mixed to a homogenous solution by stirring at ambient temperature, then stored in a closed vessel.

EXAMPLE VII

| Ingredient | Amount (wt./wt., Parts per hundred) |
| --- | --- |
| polyvinyl pyrrolidone/vinyl acetate | 48.00 |
| ethyl alcohol | 52.35 |
| propylene glycol | 2.00 |
| pentahexylmethylene biguanide hydrochloride | 1.00 |
| F. D. and C. red No. 40 | 0.05 |

The ingredients were thoroughly mixed to a homogeneous solution by stirring at ambient room temperature, then stored in a closed vessel.

EXAMPLE VIII

| Ingredient | Amount (wt./wt., Parts Per Hundred) |
| --- | --- |
| polyvinyl pyrrolidone/vinyl acetate copolymer | 48.00 |
| ethyl alcohol | 48.98 |
| propylene glycols | 2.00 |
| $N,N^1$-(1,10-decanediyldi-1[4H]-pyridinyl-4-)-(1-octanamine) dihydrochloride | 1.00 |
| D. and C. Red No. 17 | 0.02 |

The ingredients were thoroughly mixed to a homogeneous solution by stirring at ambient room temperature then stored in a closed vessel.

EXAMPLE IX

| Ingredient | Amount (wt./wt., Parts Per Hundred) |
| --- | --- |
| polyvinyl pyrrolidone/vinyl acetate copolymer | 49.00 |
| ethyl alcohol | 46.80 |
| iodine | 0.20 |
| propylene glycol | 4.00 |

The ingredients were thoroughly mixed to a homogeneous solution by stirring at ambient room temperature, then stored in a closed vessel.

EXAMPLE X

| Ingredient | Amount (wt./wt., Parts Per Hundred) |
| --- | --- |
| ethyl cellulose | 3.50 |
| propylene glycol methyl ether | 15.00 |
| isopropyl alcohol | 79.00 |
| polyoxypropylene glycol L-101 | 2.00 |
| Polyoxypropylene glycol L-31 | 0.30 |
| iodine | 0.20 |

The ingredients were thoroughly mixed to a homogeneous solution by stirring at ambient temperature, then stored in a closed vessel.

EXAMPLE XI

| Ingredient | Amount (wt./wt., Parts Per Hundred) |
| --- | --- |
| ethyl cellulose | 3.5 |
| propylene glycol methyl ether | 30.00 |
| p-chloro-m-xylenol | 1.75 |
| polyoxypropylene glycol L-101 | 2.00 |
| polyoxypropylene glycol L-30 | 0.30 |
| Drug and Cosmetic Red No. 17 | 0.04 |

The ingredients wee thoroughly mixed to a homogeneous solution by stirring at ambient room temperature, then stored in a closed vessel.

Several evaluations were conducted on sections of film prepared from the above example compositions. The films were formed by placing about ten ml of the compositions in aluminum pans (7.5 cm by 12.5 cm) to allow the fugitive solvent to evaporate at ambient temperature.

The films formed were carefully removed intact from the pans and divided into sections for testing.

A standard test of antimicrobial efficacy is a determination of the zone of inhibition of growth of a microorganism around a sample of the antimicrobial agent on a culture plate seeded with the microorganisms. The larger the zone of inhibition for a given amount of a particular antimicrobial agent, the greater the efficacy of the agent. The antimicrobial agent was chlorhexidine diacetate in example compositions II–VI with a concentration of was one part in one hundred (wt./wt.), thus any variability in the zone of inhibition with compositions II–VI is a result of the availability of the chlorhexidine diacetate from the film. Example compositions VII–XI include alternative film forming materials and antimicrobial agents. The zone of inhibition results are shown in Table II.

TABLE II

| Composition No. | Inhibition Zone (mm × mm) | | | |
|---|---|---|---|---|
| | S. Aureus | P. Aeruginosa | E. Coli | Cand. Albicans |
| I (Control) | 0 | 0 | 0 | 0 |
| II | 4.0 × 4.3 | 3.5 × 4.0 | 3.0 × 3.3 | 5.3 × 5.5 |
| III | 2.8 × 3.0 | 2.2 × 2.6 | 2.0 × 2.2 | 2.3 × 2.3 |
| IV | 3.0 × 3.0 | 1.6 × 2.1 | 2.5 × 2.0 | 3.5 × 3.3 |
| V | 4.8 × 4.5 | 4.0 × 4.3 | 2.5 × 3.3 | 4.5 × 5.3 |
| VI | 4.0 × 3.8 | 4.0 × 3.3 | 3.3 × 3.5 | 4.0 × 4.5 |
| VII | 2.0 × 3.0 | 1.5 × 1.0 | 1.5 × 1.5 | 5.0 × 7.0 |
| VIII | 3.0 × 3.0 | 2.0 × 1.5 | 1.5 × 1.0 | 2.5 × 5.0 |
| IX | 8.5 × 5.5 | not done | 1.0 × 1.0 | 16.5 × 12.0 |
| X | 8.0 × 7.0 | not done | 7.0 × 6.0 | 3.0 × 4.0 |
| XI | 1.25 × 2.25 | 0 × 0 | not done | not done |

The film samples used in the test were substantially equivalent in size (about 8 mm×8 mm). As a control, composition I had a low level of antimicrobial agent (0.12 parts per hundred) and castor oil, a hydrophobic plasticizer, and as a result, shows no zone of inhibition with any of the tested microorganisms. All of the other compositions show sufficient antimicrobial activity to function effectively for surgical site preparation. The differences in size of the inhibition zone are related to the availability and the properties of the antimicrobial agent from the film. In the compositions Nos. III and IV, the agent is chlorhexidine diacetate with a hydrophobic plasticizing agent, i.e., cottonseed and castor oils respectively. The zones of inhibition for compositions Nos. III and IV are somewhat smaller than the compositions (Nos. II, V and VI) with chlorhexidine diacetate where the plasticizers are hydrophilic, i.e., polyoxypropylene glycol, glycerin and poly(tetrahydrofuran) respectively. In the compositions with hydrophilic plasticizers, the zones of inhibition are generally larger for most of the microorganisms. In the compositions IX and X, where the antimicrobial agent is iodine, large inhibition zones are seen, but the dye indicator system may not be used because the material is inherently colored. In composition XI, the antimicrobial agent, p-chloro-m-xylenol, is not as effective on the test organisms as the chlorhexidine diacetate at the concentration present in the sample.

The larger zones of inhibition, while indicative of a sustained efficacy of the antimicrobial agent, are not the only factors which are important for a composition intended for surgical site preparation. The composition must also rapidly release sufficient antimicrobial agent to substantially eliminate microorganisms normally present on the skin so as not to infect the open surgical wound. Two other studies were conducted on the several example compositions I–VI which have chlorhexidine diacetate as the antimicrobial agent. These studies demonstrated the rate of release of the antimicrobial agent is faster when the plasticizing agent is hydrophilic and slower when the plasticizing agent is hydrophobic. A high performance liquid chromatographic (HPLC) analysis was performed on aliquots of ambient temperature aqueous extraction samples of the several chlorhexidine diacetate containing compositions listed in Table I. The initial HPLC aliquots were taken from the stirred extraction vessel at 1, 3, 5 and 8 minutes after introduction of the film specimen into the extraction vessel. Following the initial sampling, the sampling intervals were lengthened and the sampling continued for 24 hours. The aliquots were assayed by HPLC using a 10 cm long $C_{18}$ silica (Nova Pak) column. The HPLC conditions included a mobile phase of aqueous 70 percent methanol containing 0.005 molar 1-pentane sulfonic acid at pH 3.5 with a flow rate of 0.7 ml/min. The standard HPLC instrument has a standard U.V. detector set at 254 nanometers.

HPLC analysis showed that example compositions I, III and IV, which had the smallest zones of inhibition, hydrophobic plasticizers and, additionally for the composition of Example I, had a lower concentration of antimicrobial agent, were statistically significantly slower to release chlorhexidine diacetate into the extraction fluid than the example compositions II, V and VI having hydrophilic plasticizers. Additionally, in the example compositions III and IV, with the hydrophobic plasticizer, the chlorhexidine diacetate concentration in the extraction fluid did not achieve a level as high as it did in the example compositions II, V and VI where the plasticizers were hydrophilic.

Further confirmation of the effects of hydrophobic and hydrophilic plasticizers was provided by a leaching analysis conducted with a flow-through sample cell mounted on a Hewlett Packard 8450A diode array spectrometer. Samples of example compositions II and IV, with chlorhexidine diacetate as the antimicrobial agent with hydrophilic and hydrophobic plasticizer, respectfully, were tested. Specimens of each of the formed films were mounted in the cell so that each was subjected to an aqueous flow at 37° C. for 24 hours. The effluent from the cell was monitored for chlorhexidine diacetate by the spectrometer. The results of the test showed that the rate of chlorhexidine diacetate leaching from the film formed with a hydrophobic plasticizer (Composition IV) was statistically significantly lower than the leaching rate from the film having the hydrophilic plasticizer (Composition II).

Based on the information presented hereinabove and a basic knowledge of properties of the several plasticizers and antimicrobial agents taught as suitable for use in the present invention, one practicing the present invention may prepare combinations of antimicrobial agents and plasticizers other than those presented in the examples which may display higher or lower relative rates of release as required for specific applications. The examples are not to be considered as limitative of the invention, but rather serve to demonstrate the ability to control the release rate from the film by adjustment to the composition. A preferred embodiment of the film forming composition which forms a film which bonds well to skin, includes the following ingredients with amounts given in parts per hundred (wt./wt.).

| Ingredient | Amount (Parts/hundred, wt./wt.) |
|---|---|
| propylene glycol methyl ether | 10 to about 50 |
| chlorhexidine diacetate | 0.5 to about 10.0 |
| ethyl cellulose | 2.5 to about 4.5 |
| polyoxypropylene glycol | 2.0 to about 4.0 |
| D. and C. red No. 17 | 0.001 to about 0.15 |
| orthophenylphenol, sodium salt | 0.1 to about 1.0 | isopropyl alcohol is added in a quantity sufficient to make 100 parts.

A composition of the present invention with a composition falling within the preferred ranges is given in Example II. Specimens of film formed from Example composition II were compared in zone of inhibition testing to a commercial product (Duraprep™, Minnesota Mining and Manufacturing, Minn. Minn.) as taught in Dell U.S. Pat. No. 5,542,012. The testing included film specimens of both materials both in an "as formed" and "washed" conditions. The Duraprep™ film product was prepared according to the manufacturer's use directions. The "as formed" samples were fleshly cast, allowed to dry, sectioned, weighed and placed on growth media seeded with microorganisms. The "washed" specimens were extracted at 37° C. in water for 24 hours to simulate efficacy of the film during the healing process subsequent to the surgical procedure. Both the "washed" and the "as formed" samples were placed on growth media seeded with microorganisms using the same technique. The results of the study are shown in Table III.

TABLE III

| Sample | Mass (mg) | Zone of inhibition (radius, mm) | |
|---|---|---|---|
| | | S. Aureus | P. Aeruginosa |
| Example No. II (as formed) | 5.9 | 6.5 | 1.5 |
| Duraprep ™ commercial product (as formed) | 7.8 | 7.5 | 0.0 |
| Example No. II (washed) | 5.9 | 2.0 | 0 |
| Duraprep ™ commercial product (washed) | 7.8 | 1.5 | 0 |

The zone of inhibition results show that a smaller mass of the present invention with the preferred composition of example composition II provides a relatively larger zone of inhibition for *S. Aureus* as well as activity against *P. Aeruginosa* than the Duraprep™ commercial film. Additionally the present invention, when washed to simulate extended use, still provides a larger zone of inhibition against *S. Aureus* than the Duraprep™ commercial product subjected to the same wash for simulating extended use.

In comparative wound healing studies of the several compositions of the present invention with chlorhexidine diacetate as the antimicrobial agent given in Table I and the current commercial Duraprep™ product conducted on weanling pigs, wound healing rates were not adversely effected by the presence of either the films of the present invention or the Duraprep™ film.

A method for preparing a skin surface as a site for a surgical procedure of the present invention includes preparing a film forming composition as a homogeneous solution of a fugitive solvent, a material for forming a film and an antimicrobial agent. The composition is then applied, preferably in overlapping concentric circles, to the skin site area selected for the surgical procedure and time allowed, generally about three to five minutes, for substantial elimination of the fugitive solvent.

Preferably the composition prepared in the preparing step includes at least one compound for indicating an area of skin covered by the composition in the applying step and for indicating substantial elimination of the fugitive solvent. Preferably the method for preparation of the skin surface includes observing a first color (purple) indicating the skin area where the composition is applied, followed by observing a second color (red) indicating the substantial elimination of the fugitive solvent.

A kit for preparing a skin surface site for a surgical procedure includes a sealed unit container containing a sufficient amount (about 10 to about 30 ml) of a film forming composition which includes a homogeneous solution in a fugitive solvent of a film forming material and an antimicrobial agent. The kit also includes applicator. The unit container and the applicator are preferably contained in a package to complete the kit. Preferably the composition includes at least one compound which provides an indication of the skin area covered by the composition and indicates the substantial elimination of the fugitive solvent.

The package for containing the unit container with the composition therein and the applicator preferably is non-resealable, thus providing a tamper-evident single use procedure kit. Preferably the container for the film forming composition is also non-resealable, further enhancing the tamper-evident properties of the kit.

What is claimed is:

1. A film forming composition for surgical site preparation on a skin surface comprising:

a fugitive solvent;

a film forming material soluble in said solvent;

an antimicrobial agent soluble in said solvent capable of being releasably retained in said film forming material;

means for providing color change indicating an area of the skin surface covered by said composition, said color change further indicating substantial elimination of said fugitive solvent from said composition after said composition is applied to the skin surface; and said film forming material and said antimicrobial agent when applied to the skin surface from said fugitive solvent, forming a substantially water insoluble, substantially tack-free flexible film adherent to the skin surface, said film capable of releasing said antimicrobial agent in a quantity sufficient to substantially inhibit microbial growth on the skin surface.

2. The composition of claim 1 further comprising a plasticizing agent for increasing the flexibility of said film.

3. The composition of claim 1 wherein said indicating means comprises at least one compound having a first color for providing a visual indication of the area of skin surface covered and a second color when said fugitive solvent is substantially eliminated, thereby providing a visual indication that said film is dry and the surgical site is ready.

4. The composition of claim 3 wherein said indicating means comprises orthophenyl phenol, sodium salt, and a quantity of a dye selected from the group consisting of Food Drug and Cosmetic Red No. 40 and Drug and Cosmetic Red No. 17, sufficient to provide a purple color on the skin surface when said fugitive solvent is present and a red color on the skin surface when said fugitive solvent is substantially eliminated.

5. The composition of claim 1 wherein said antimicrobial agent is present in a quantity sufficient to substantially inhibit microbial growth on the surface of skin, said agent being selected from the group consisting of iodophors, chlorophenols, biguanides, antibiotics and biologically active salts thereof.

6. The composition of claim 6 wherein said antimicrobial agent is chlorhexidine diacetate present in a quantity ranging between about 0.5 to about 10 parts per one hundred parts (weight/weight).

7. A film forming composition for surgical site preparation on a skin surface comprising:

a fugitive solvent;

a film forming material soluble in said solvent;

an antimicrobial agent soluble in said solvent capable of being releasably retained in said film forming material;

means for indicating an area of the skin surface being covered by said composition and for indicating substantial elimination of said fugitive solvent from said composition afer said composition is applied to the skin surface; and said composition forming a substantially tack-free, substantially water insoluble, flexible film adherent to the skin surface, said film having a first color when said solvent is present thereby indicating the covered area of the skin surface and a second color when said solvent is substantially eliminated, thereby providing an indication that said film is dry and the surgical site is ready.

8. The composition of claim 7 wherein said fugitive solvent is selected from the group consisting of isopropanol, ethanol, ethylene dichloride, acetone, ethyl acetate and 1,1, 2-trichlorotrifluoroethane.

9. The composition of claim 7 wherein said film forming material is selected from the group consisting of ethyl cellulose, methoxy cellulose, hydroxyethyl cellulose, polyvinyl pyrrolidone, vinyl acetate, and cross linked pyrrolidone.

10. The composition of claim 7 wherein said film forming material is ethyl cellulose having an ethoxy content between about 45 percent to about 55 percent (weight/weight).

11. The composition of claim 7 further comprising a plasticizing agent for increasing the flexibility of said film selected from the group consisting of polyethylene glycol, polyoxypropylene glycol, polyoxyethylenepropylene glycol, glycerin, polyoxyethylene-polyoxypropylene block copolymers, cottonseed oil, palm oil, rapeseed oil, sunflower oil, castor oil and poly(tetrahydrofuran).

12. The composition of claim 7 wherein said antimicrobial agent is present in a quantity sufficient to substantially inhibit microbial growth on the surface of the skin and is selected from the group consisting of iodophors, chlorophenols, biguanides, antibiotics and biologically active salts thereof.

13. The composition of claim 7 wherein said indicating means comprises orthophenylphenol, sodium salt, and a quantity of a dye selected from the group Food, Drug and Cosmetic Red No. 40 and Drug and Cosmetic Red No. 17, sufficient to provide a purple color on the skin surface when said fugitive solvent is present and a red color on the skin surface when said fugitive solvent is substantially eliminated.

14. A method for preparing skin as a site for a surgical procedure comprising:
   preparing a film forming composition as a homogenous solution of a fugitive solvent, a material for forming a film, means for providing color change indicating an area of skin surface covered by said composition, said color change further indicating substantial elimination of said fugitive solvent, and an antimicrobial agent;
   applying said composition to the skin site selected for the surgical procedure; and
   allowing elimination of said fugitive solvent.

15. The method of claim 14 further comprising observing a first color indicating the site having said composition applied thereon and observing a second color after said allowing step thereby indicating said substantial elimination of said fugitive solvent.

16. A film forming composition for preparing skin as a site for a surgical procedure comprising a homogeneous solution of:

| Ingredient | Amount (Parts/Hundred, {wt./wt.}) |
|---|---|
| propylene glycol methyl ether | about 10 to about 50 |
| ethyl cellulose | about 2.5 to about 4.5 |
| polyoxypropylene glycol | about 2 to about 4 |
| Drug and Cosmetic red no. 17 | about 0.001 to about 0.015 |
| orthophenyl phenol, sodium salt | about 0.1 to about 1.0 |
| chlorhexidine diacetate | about 0.5 to about 10 |
| isopropyl alcohol | quantity sufficient to make 100 parts; | said composition for application to a skin surface from said isopropyl alcohol as a fugitive solvent;

said ethyl cellulose, propylene glycol methyl ether and polyoxypropylene glycol forming a skin adherent flexible film capable of releasably containing said chlorhexidine diacetate as an antimicrobial agent, thereby forming a substantially water insoluble, substantially tack-free flexible film;

said Drug and Cosmetic red No. 17 and said orthophenyl phenol, sodium salt, providing said composition a first color indicating an area of the skin surface covered and a second color indicating substantial elimination of said fugitive solvent after said composition is applied to the skin surface; and said antimicrobial agent being releaseably retained in said film and capable of being released in a quantity sufficient for substantially inhibiting microbial growth on the skin surface.

17. A kit for preparing a skin surface site for a surgical procedure comprising:
   a sealed unit container for containing the film forming composition of claim 1
   means for applying said film forming composition to a skin surface; and
   a package holding said sealed unit container and said means for applying.

18. The kit of claim 17 wherein said film forming composition comprises ethyl cellulose, propylene glycol methyl ether, polyoxypropylene glycol, chlorhexidine diacetate and isopropyl alcohol.

19. The kit of claim 18 wherein said film forming composition further comprises sufficient orthophenyl phenol, sodium salt, and Drug and Cosmetic red no. 17 to provide a purple color on the skin surface when said fugitive solvent is present and a red color on the skin surface when said fugitive solvent is substantially eliminated.

20. The kit of claim 17 wherein said sealed unit container and said package are non-resealable after opening, thereby providing a single-use procedure kit for surgical site preparation.

\* \* \* \* \*